US008453650B1

(12) United States Patent
Frey

(10) Patent No.: US 8,453,650 B1
(45) Date of Patent: Jun. 4, 2013

(54) MOUTHPIECE

(75) Inventor: David Scott Frey, Los Angeles, CA (US)

(73) Assignee: MDM, Beverly Hills, CA (US)

(*) Notice: Subject to any disclaimer, the term of this patent is extended or adjusted under 35 U.S.C. 154(b) by 4 days.

(21) Appl. No.: 13/541,209

(22) Filed: Jul. 3, 2012

(51) Int. Cl.
*A61C 5/14* (2006.01)
*A61F 5/56* (2006.01)

(52) U.S. Cl.
USPC .......... 128/859; 128/848; 128/861; 128/862; 433/6; 602/902

(58) Field of Classification Search
USPC ............... 128/859, 861–862, 848; 433/6, 41, 433/45, 47, 7, 19, 34, 37–39, 71, 214
See application file for complete search history.

(56) References Cited

U.S. PATENT DOCUMENTS

| 257,038 | A | 4/1882 | McMann |
| 1,117,928 | A | 11/1914 | Thurmond |
| 1,323,832 | A | 12/1919 | Chige |
| 1,461,209 | A | 7/1923 | Bridges |
| 1,470,888 | A | 10/1923 | Smedley |
| 1,487,392 | A | 3/1924 | Lee |
| 2,118,980 | A | 5/1938 | Montgomery |
| 2,257,709 | A | 9/1941 | Anderson |
| 2,423,005 | A | 6/1947 | Chaiken |
| 2,630,117 | A | 3/1953 | Coleman |
| 2,643,652 | A | 6/1953 | Cathcart |
| 2,659,366 | A | 11/1953 | Savarese |
| 2,669,988 | A | 2/1954 | Carpenter |
| 2,678,043 | A | 5/1954 | Stark |
| 2,694,397 | A | 11/1954 | Herma |
| 2,702,032 | A | 2/1955 | Freedland |
| 2,708,931 | A | 5/1955 | Freedland |
| 2,750,941 | A | 6/1956 | Cathcart |

(Continued)

FOREIGN PATENT DOCUMENTS

| CA | 1147583 | 7/1983 |
| DE | 480423 | 8/1929 |
| EP | 1398061 A2 | 3/2004 |

OTHER PUBLICATIONS

Arent, et al., "Effects of a neuromuscular dentistry-designed mouthguard on muscular endurance and anaerobic power," Comparative Exercise Phsiology 7(2); 73-79, Cambridge University Press 2010.

(Continued)

*Primary Examiner* — Patricia Bianco
*Assistant Examiner* — Kari Petrik
(74) *Attorney, Agent, or Firm* — Greenberg Traurig, LLP

(57) ABSTRACT

A mouthpiece includes a first body configured to be secured over one or more teeth of a user. The first body comprises a frame for location about at least one of a molar or a premolar of user, as a first bite pad between upper teeth and lower teeth. The first bite pad is molded in the frame while in situ in the mouth of the user and the first bite pad is formed by a PVS material. The first bite pad is in contact with at least one of a molar or a premolar of user, and the first bite pad defines an exterior shape of at least a portion of the teeth of a user. There is a similar second body with a connector between the first body and the second body and together these form the appliance for the user.

13 Claims, 11 Drawing Sheets

U.S. PATENT DOCUMENTS

| | | | |
|---|---|---|---|
| 2,833,278 A * | 5/1958 | Ross | 128/862 |
| 2,847,003 A | 8/1958 | Helmer | |
| 2,933,811 A | 4/1960 | Lifton | |
| 2,966,908 A | 1/1961 | Cathcart | |
| 3,016,052 A | 1/1962 | Zubren | |
| 3,058,462 A | 10/1962 | Greenblum | |
| 3,073,300 A | 1/1963 | Berghash | |
| 3,082,765 A | 3/1963 | Helmer | |
| 3,107,667 A | 10/1963 | Moore | |
| 3,124,129 A | 3/1964 | Grossberg | |
| 3,126,002 A | 3/1964 | Owens | |
| 3,203,417 A | 8/1965 | Helmer | |
| 3,207,153 A | 9/1965 | Goldstein | |
| 3,222,085 A | 12/1965 | Gores et al. | |
| 3,247,844 A | 4/1966 | Berghash | |
| 3,312,218 A | 4/1967 | Jacobs | |
| 3,319,626 A | 5/1967 | Lindsay | |
| 3,407,809 A | 10/1968 | Ross | |
| 3,411,501 A | 11/1968 | Greenberg | |
| 3,416,527 A | 12/1968 | Hoef | |
| 3,448,738 A | 6/1969 | Berghash | |
| 3,457,916 A | 7/1969 | Wolicki | |
| 3,485,242 A | 12/1969 | Greenberg | |
| 3,496,936 A | 2/1970 | Gores | |
| 3,505,995 A | 4/1970 | Greenberg | |
| 3,513,838 A | 5/1970 | Foderick et al. | |
| 3,518,988 A | 7/1970 | Gores | |
| 3,532,091 A | 10/1970 | Lerman | |
| 3,682,164 A | 8/1972 | Miller | |
| 3,692,025 A | 9/1972 | Greenberg | |
| 3,768,465 A | 10/1973 | Helmer | |
| 3,864,832 A | 2/1975 | Carlson | |
| 3,916,527 A | 11/1975 | Linkow | |
| 3,924,638 A | 12/1975 | Mann | |
| 3,943,924 A | 3/1976 | Kallestad et al. | |
| 4,030,493 A | 6/1977 | Walters et al. | |
| 4,044,762 A | 8/1977 | Jacobs | |
| 4,063,552 A | 12/1977 | Going et al. | |
| 4,114,614 A | 9/1978 | Kesling | |
| 4,185,817 A | 1/1980 | Peterson | |
| 4,211,008 A | 7/1980 | Lerman | |
| 4,330,272 A | 5/1982 | Bergersen | |
| 4,337,765 A | 7/1982 | Zimmerman | |
| 4,348,178 A | 9/1982 | Kurz | |
| 4,376,628 A | 3/1983 | Aardse | |
| 4,457,708 A | 7/1984 | Dufour | |
| 4,490,112 A | 12/1984 | Tanaka et al. | |
| 4,495,945 A | 1/1985 | Liegner | |
| 4,519,386 A | 5/1985 | Sullivan | |
| 4,568,280 A | 2/1986 | Ahlin | |
| 4,591,341 A | 5/1986 | Andrews | |
| 4,640,273 A | 2/1987 | Greene | |
| 4,671,766 A | 6/1987 | Norton | |
| 4,672,959 A | 6/1987 | May | |
| 4,727,867 A | 3/1988 | Knoderer | |
| 4,755,139 A | 7/1988 | Abbatte et al. | |
| 4,763,791 A | 8/1988 | Halverson et al. | |
| 4,765,324 A | 8/1988 | Lake, Jr. | |
| 4,791,941 A | 12/1988 | Schaefer | |
| 4,793,803 A | 12/1988 | Martz | |
| 4,799,500 A | 1/1989 | Newbury | |
| 4,810,192 A | 3/1989 | Williams | |
| 4,838,283 A | 6/1989 | Lee, Jr. | |
| 4,848,365 A | 7/1989 | Guarlotti et al. | |
| 4,867,147 A | 9/1989 | Davis | |
| 4,944,947 A | 7/1990 | Newman | |
| 4,955,393 A | 9/1990 | Adell | |
| 4,976,618 A | 12/1990 | Anderson | |
| 4,977,905 A | 12/1990 | Kittelsen et al. | |
| 4,989,616 A | 2/1991 | Lee, Jr. | |
| 5,031,611 A | 7/1991 | Moles | |
| 5,031,638 A | 7/1991 | Castaldi | |
| 5,063,940 A | 11/1991 | Adell et al. | |
| 5,076,785 A | 12/1991 | Tsai | |
| 5,082,007 A | 1/1992 | Adell | |
| 5,103,838 A | 4/1992 | Yousif | |
| 5,112,225 A | 5/1992 | Diesso | |
| 5,117,816 A | 6/1992 | Shapiro et al. | |
| D328,494 S | 8/1992 | Schwendeman et al. | |
| 5,152,301 A | 10/1992 | Kittelsen et al. | |
| 5,154,609 A | 10/1992 | George | |
| 5,165,424 A | 11/1992 | Silverman | |
| 5,174,284 A | 12/1992 | Jackson | |
| 5,194,003 A | 3/1993 | Garay et al. | |
| 5,194,004 A | 3/1993 | Bergersen | |
| 5,203,351 A | 4/1993 | Adell | |
| 5,234,005 A | 8/1993 | Kittelsen | |
| 5,235,991 A | 8/1993 | Minneman | |
| 5,259,762 A | 11/1993 | Farrell | |
| 5,277,203 A | 1/1994 | Hays | |
| D343,928 S | 2/1994 | Kittelsen | |
| 5,293,880 A | 3/1994 | Levitt | |
| 5,297,960 A | 3/1994 | Burns | |
| 5,299,936 A | 4/1994 | Ueno | |
| 5,302,117 A | 4/1994 | Kraut et al. | |
| 5,313,960 A | 5/1994 | Tomasi | |
| 5,316,474 A | 5/1994 | Robertson | |
| 5,320,114 A | 6/1994 | Kittelsen et al. | |
| 5,323,787 A | 6/1994 | Pratt | |
| 5,328,362 A | 7/1994 | Watson et al. | |
| 5,336,086 A | 8/1994 | Simmen et al. | |
| 5,339,832 A | 8/1994 | Kittelsen et al. | |
| 5,353,810 A | 10/1994 | Kittelsen et al. | |
| 5,365,946 A | 11/1994 | McMillan | |
| 5,385,155 A | 1/1995 | Kittelsen et al. | |
| 5,386,821 A | 2/1995 | Poterack | |
| D356,188 S | 3/1995 | Kittelsen | |
| 5,401,234 A | 3/1995 | Libin | |
| 5,406,963 A | 4/1995 | Adell | |
| 5,447,168 A | 9/1995 | Bancroft | |
| 5,460,527 A | 10/1995 | Kittelsen | |
| 5,469,865 A | 11/1995 | Minneman | |
| 5,490,520 A | 2/1996 | Schaefer et al. | |
| 5,511,562 A | 4/1996 | Hancock | |
| 5,513,656 A | 5/1996 | Boyd, Sr. | |
| 5,533,524 A | 7/1996 | Minneman | |
| D373,421 S | 9/1996 | Brown | |
| 5,566,684 A | 10/1996 | Wagner | |
| 5,584,687 A | 12/1996 | Sullivan | |
| 5,586,562 A | 12/1996 | Matz | |
| 5,590,643 A | 1/1997 | Flam | |
| 5,592,951 A | 1/1997 | Castagnaro et al. | |
| 5,624,257 A | 4/1997 | Farrell | |
| 5,636,379 A | 6/1997 | Williams | |
| 5,646,216 A | 7/1997 | Watson et al. | |
| 5,649,534 A | 7/1997 | Briggs, III | |
| 5,666,973 A | 9/1997 | Walter | |
| 5,692,523 A | 12/1997 | Croll | |
| 5,718,243 A | 2/1998 | Weatherford et al. | |
| 5,718,575 A | 2/1998 | Cross, III | |
| 5,730,599 A | 3/1998 | Pak | |
| 5,746,221 A | 5/1998 | Jones et al. | |
| D397,442 S | 8/1998 | Kittelsen | |
| 5,816,255 A | 10/1998 | Fishman et al. | |
| 5,819,744 A | 10/1998 | Stoyka, Jr. | |
| 5,823,193 A | 10/1998 | Singer et al. | |
| 5,823,194 A | 10/1998 | Lampert | |
| 5,826,581 A | 10/1998 | Yoshida | |
| 5,836,761 A * | 11/1998 | Belvedere | 433/6 |
| 5,865,619 A | 2/1999 | Cross | |
| 5,873,365 A | 2/1999 | Brown | |
| 5,879,155 A | 3/1999 | Kittelsen | |
| 5,915,385 A | 6/1999 | Hakimi | |
| 5,921,240 A | 7/1999 | Gall | |
| 5,931,164 A | 8/1999 | Kiely et al. | |
| 5,947,918 A | 9/1999 | Jones et al. | |
| 5,970,981 A | 10/1999 | Ochel | |
| 6,012,919 A | 1/2000 | Cross | |
| 6,036,487 A | 3/2000 | Westerman | |
| 6,039,046 A | 3/2000 | Swartz et al. | |
| 6,068,475 A | 5/2000 | Stoyka, Jr. | |
| 6,082,363 A | 7/2000 | Washburn | |
| 6,092,524 A | 7/2000 | Barnes, Sr. | |
| 6,098,627 A | 8/2000 | Kellner et al. | |
| 6,109,266 A | 8/2000 | Turchetti | |

| | | |
|---|---|---|
| 6,257,239 B1 | 7/2001 | Kittelsen et al. |
| 6,527,549 B1 * | 3/2003 | Berzins ............................ 433/45 |
| 7,101,178 B2 * | 9/2006 | Diesso ............................. 433/37 |

OTHER PUBLICATIONS

Staplemann, et al., "The NTI-tss device for the therapy of bruxism, temporamandibular disorders, and headache—Where do we stand? A qualitative systematic review of the literature," BMC Oral Health 2008.

Bender, Steven, "Occlusion, Function, and Parafunction: Understanding the Dynamics of a Healthy Stomatagnathic System," ADA CERP, 2009.

1-800-Dentist information regarding NTI Appliance and migraines, 2012.

* cited by examiner

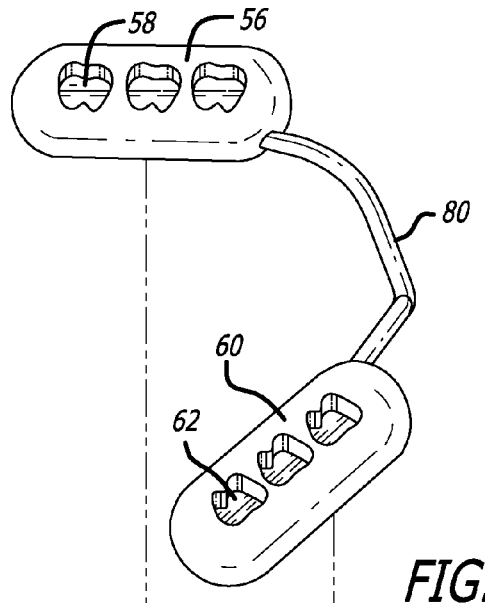
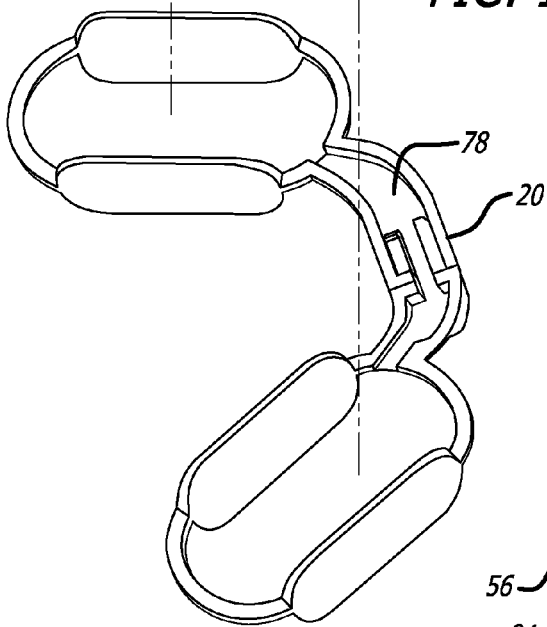
FIG. 10A
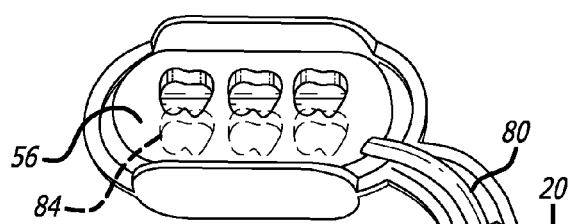
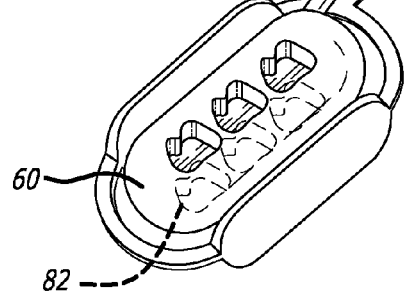
FIG. 10B

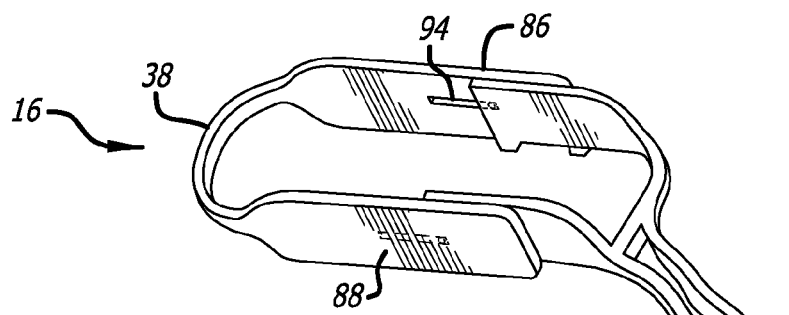
*FIG. 11A*
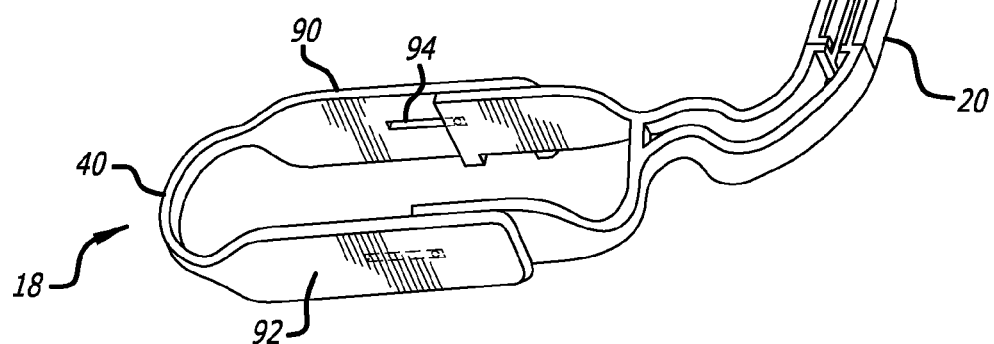
*FIG. 11B*
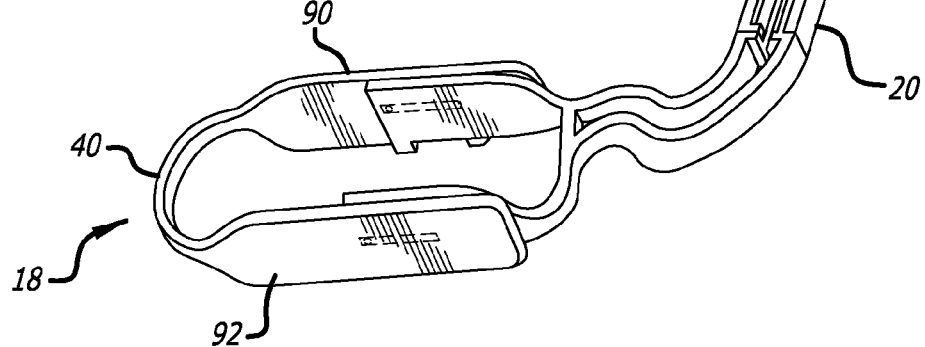

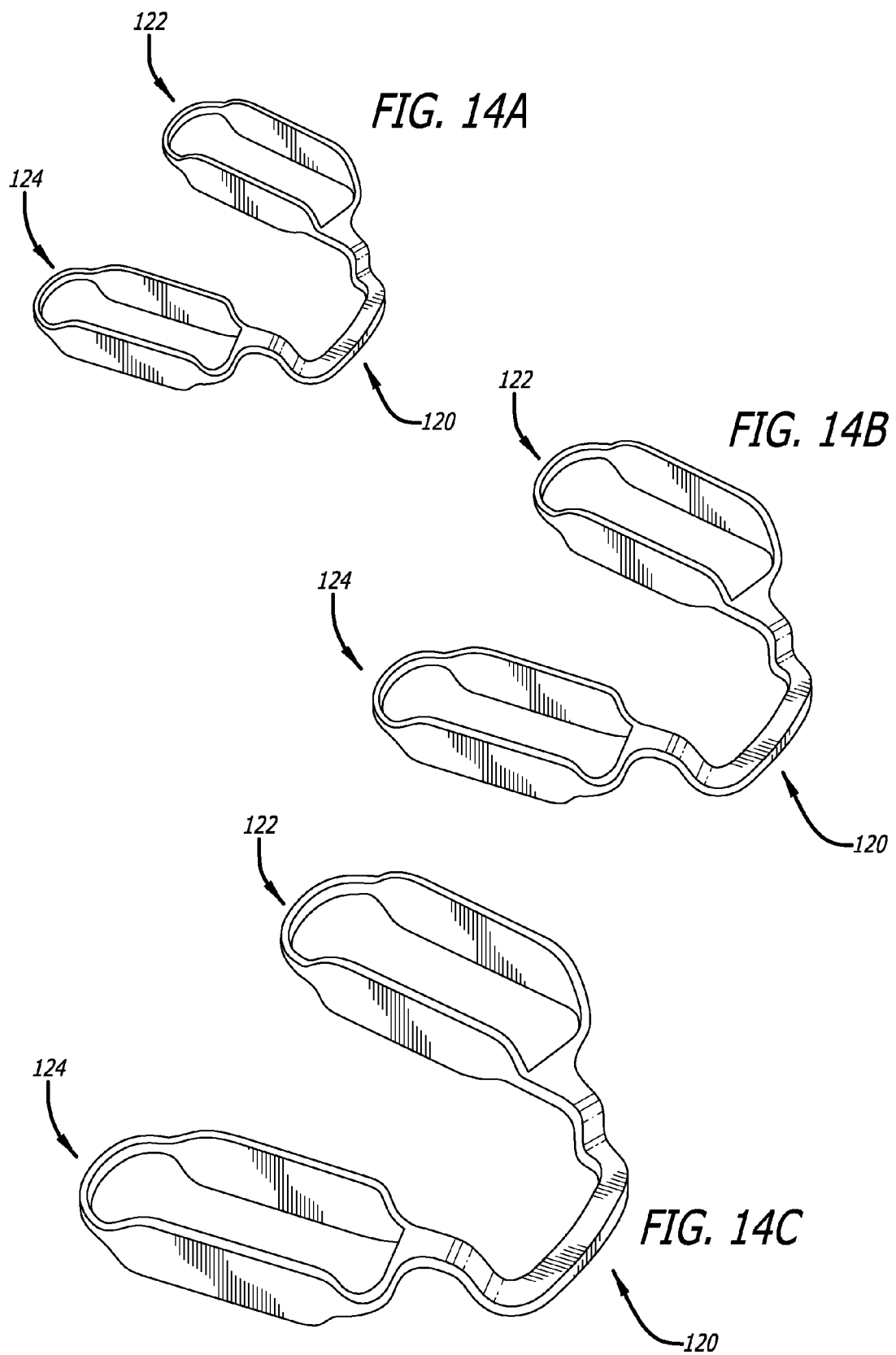

MOUTHPIECE

FIELD OF DISCLOSURE

This disclosure relates to mouthpieces. In particular, the disclosure concerns oral devices for spacing the occlusal surfaces of the teeth of a user. This spacing, when in the correct position, can prevent concussions, enhance athletic ability, improve sleep, and reduce headaches and temporomandibular disorders.

BACKGROUND

Different mouthpieces or mouthguards are known. They all have a disadvantage in relation to the form and complexity of forming good fits for each mouth, and in the nature of forming what should be regarded as the best fit to improve the prevention of clenching of the mouth when this should be avoided, and minimize concussion during high impact.

There is a need for a mouthpiece and mouthguard, and a method of forming such a mouthpiece and mouthguard, which overcomes the disadvantages of known mouthpieces and mouthguards that is better than existing mouthguards and methods of making these mouthguards.

There is also a need to assist in attaining the MORA effect or an orthopedic location, a harmonious neuromuscular balance of the muscles of the jaw, teeth and jaw joint (tmj) that translates into increased strength, balance and flexibility for each user. Current devices do not easily achieve this.

Many athletes strive to be the best they can be. They eat right, they work out, and they take vitamin supplementation. However, if they are structurally out of alignment, they will struggle harder and work harder to achieve optimum results. The average human head weighs ten pounds. This is the weight of an average bowling ball. This "bowling ball" sits forward of our bodies and the muscles must maintain our heads over our bodies. Releasing some of the load the body is using to hold one's head helps to alleviate stress on the central nervous system (cns), which translates into the burst of energy, better balance, and increased flexibility that patients are experiencing. This theory has been supported by many scientific journals specifically: Arent, Shawn, McKenna, Jennifer, and Golem, Devon (2010) *Effects of a neuromuscular dentistry-designed mouthguard on muscular endurance and anaerobic power*. Comparative Exercise Physiology 7(2); 73-79; Cambridge University Press. The contents of this study are incorporated by reference herein.

SUMMARY OF THE DISCLOSURE

The disclosed mouthpiece is designed to help the individual achieve an optimized physiological position.

An oral appliance for a user comprises the following components.

A first body is configured to be secured over one or more teeth of a user. The first body comprises a frame for location about at least one of a molar a premolar of user, and a first bite pad between upper teeth and lower teeth. In one form, the location of the frame lays over the molars and premolars of the lower and upper teeth and is hollow in the center. The first bite pad is molded in the frame while in situ in the mouth of the user and the first bite pad is formed by a PVS material. The first bite pad is in contact with at least one of a molar a premolar of user, and the first bite pad defines an exterior shape of at least a portion of the teeth of a user.

A second body is configured to be secured over one or more teeth of a user. The second body comprises a frame for location about at least one of a molar a premolar of user, a second bite pad between upper teeth and lower teeth. The second bite pad is molded in the frame while in situ in the mouth of the user and the second bite pad is formed by a PVS material. The second bite pad is in contact with at least one of a molar a premolar of user. In one form, the location of the frame lays over the molars and premolars of the lower and upper teeth and is hollow in the center. In one form, the location of the frame lays over the molars and premolars of the lower and upper teeth and is hollow in the center. The second bite pad defines an exterior shape of at least a portion of the teeth of a user.

There is a connector between the first frame and the second frame thereby connecting the first body and second body together and forming with the first body and second body the appliance for the user.

A device, methods and kit in accordance with the present disclosure may resolve many of the needs and shortcomings of known devices and method and provide additional improvements and advantages.

The disclosed mouthguard prevents the completion of the clenching mechanism, and is comfortable and unobtrusive and does not impede breathing or speaking.

The custom manufacture of oral appliances based on the users' teeth is attained. The custom manufacture is not laborious and expensive, and is simple and the manufacture of the oral appliance in reduced the time and effort and with great accuracy is possible. Adequate fit and comfort is thereby attained.

BRIEF DESCRIPTION OF THE DRAWINGS

In order to further explain the characteristics of the disclosure, the following embodiments of an improved oral appliance according to the disclosure are given as an example only, without being limitative in any way, with reference to the accompanying drawings, in which:

FIG. 10A shows a first alternative oral appliance product and the separable frames used for making the oral appliance product.

FIG. 10B shows an opposite view of the first alternative oral appliance product and the separable frames used for making the oral appliance product, with the PVS formed portions of the appliance product in the frames.

FIG. 11A shows a second alternative oral appliance product with the separable frames used for making the oral appliance product with extended frames.

FIG. 11B shows a view of the second alternative oral appliance product and the separable frames used for making the oral appliance product with contracted frames.

FIGS. 14A, 14B and 14C are perspective views showing an integrated single piece form of device with the first and second bodies, and also showing the frame, in respectively each of three different sizes: small, medium and large and can be part of the kit.

Figure 1:
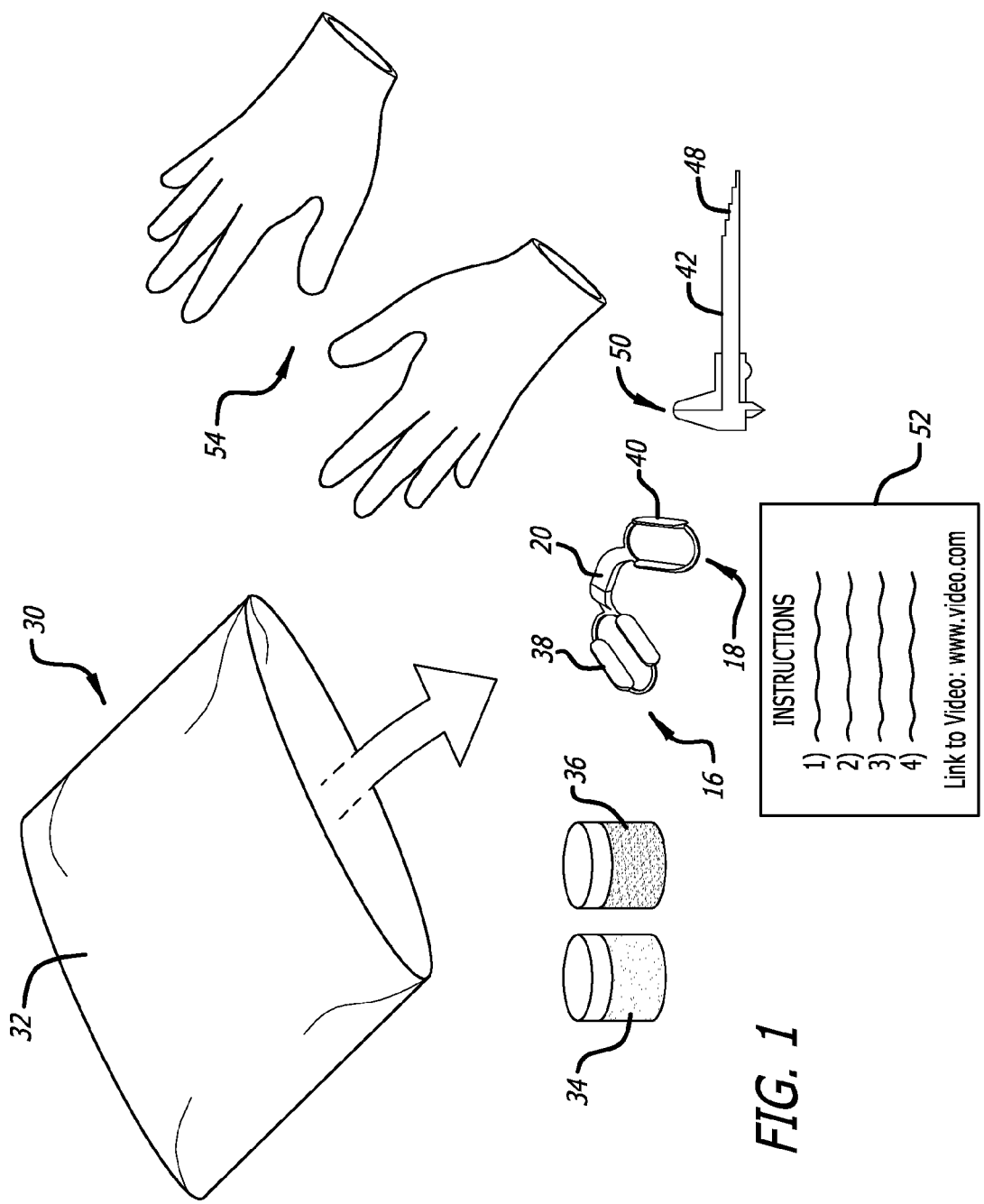
FIG. 1 illustrates a kit with two different PVS substances, for instance, poly vinyl siloxane base and catalyst, the frame of the mouth guard, calipers for measuring teeth to see how much space is needed, and instruction with a link to a video and a pair of gloves.
Figure 2:
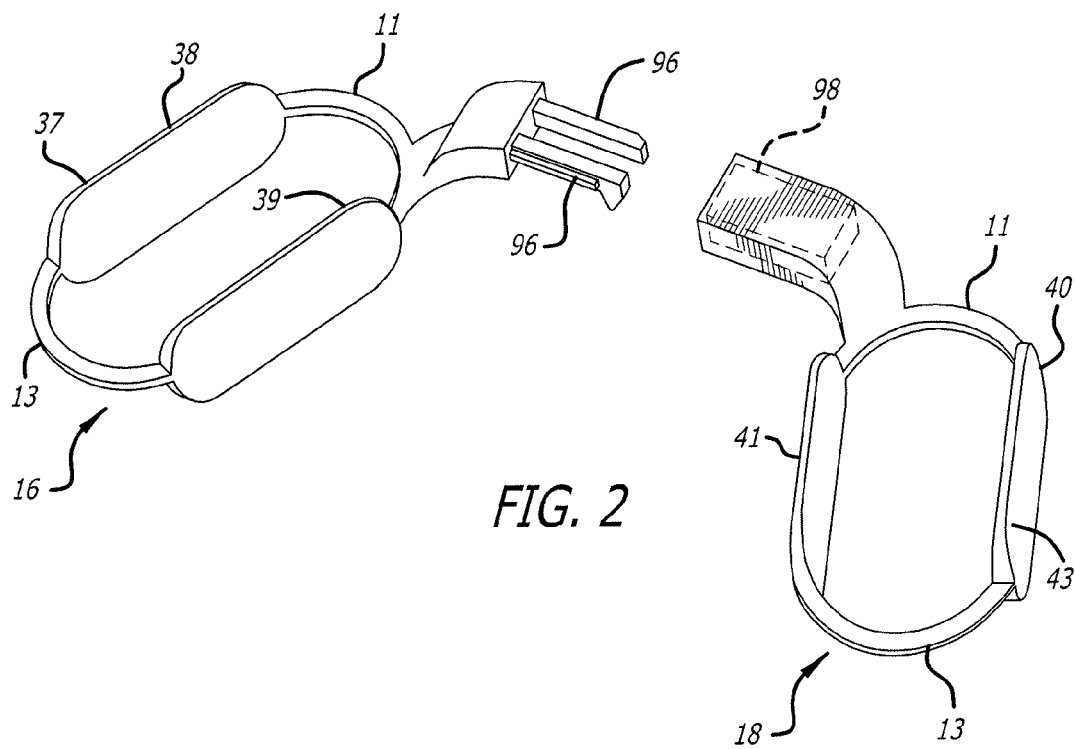
FIG. 2 is perspective view of separation of the first and second bodies, including the frame and connector.
Figure 3:
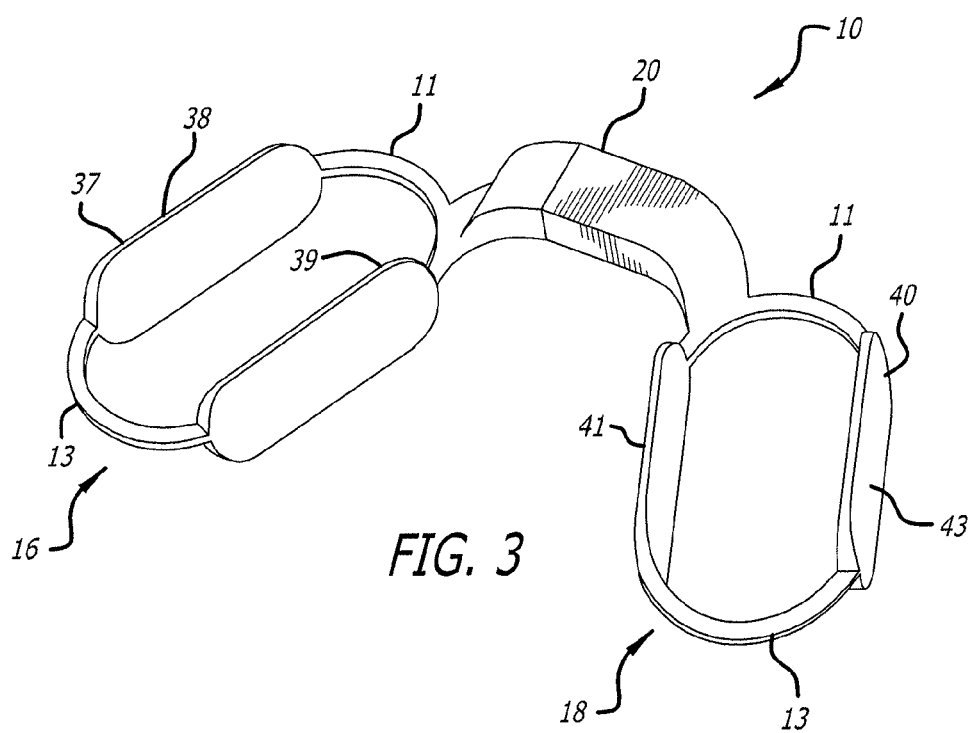
FIG. 3 is perspective view of the connected first and second bodies, including the frame and connector.
Figure 4:
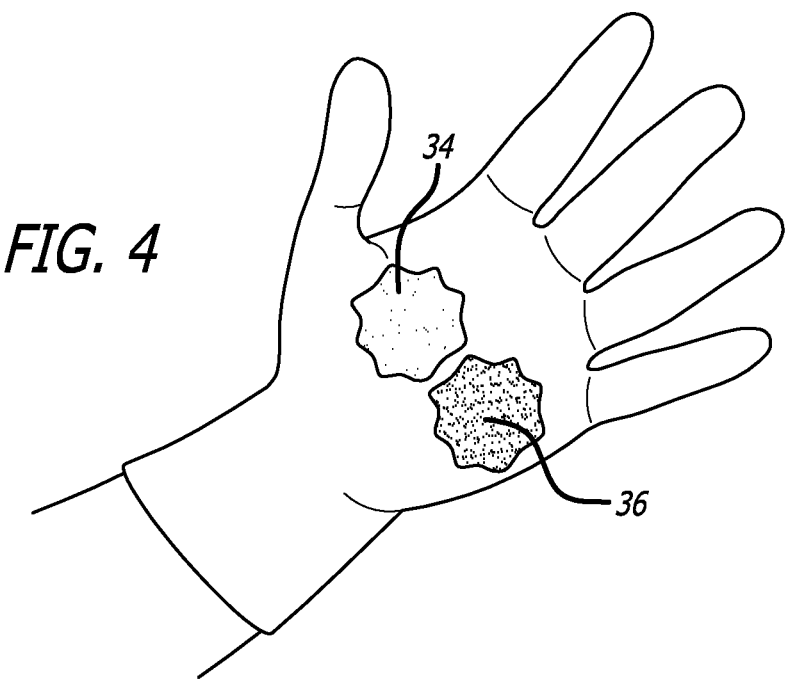
FIG. 4 shows the 2 different epoxies poly vinyl siloxane base and catalyst, separately in the gloved hand.
Figure 5:
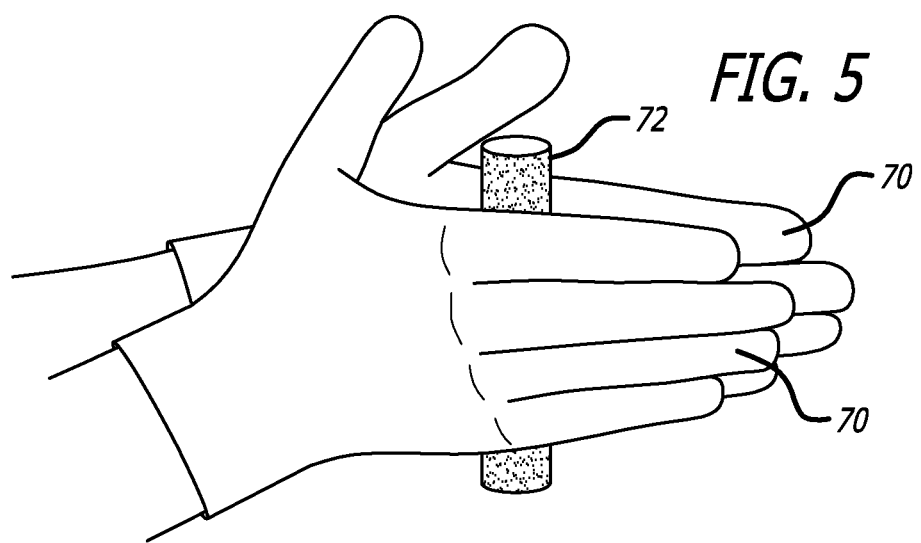
FIG. 5 shows the 2 different epoxies poly vinyl siloxane base and catalyst between the gloved hand being mixed together and then rolling it out like a log.
Figure 6:
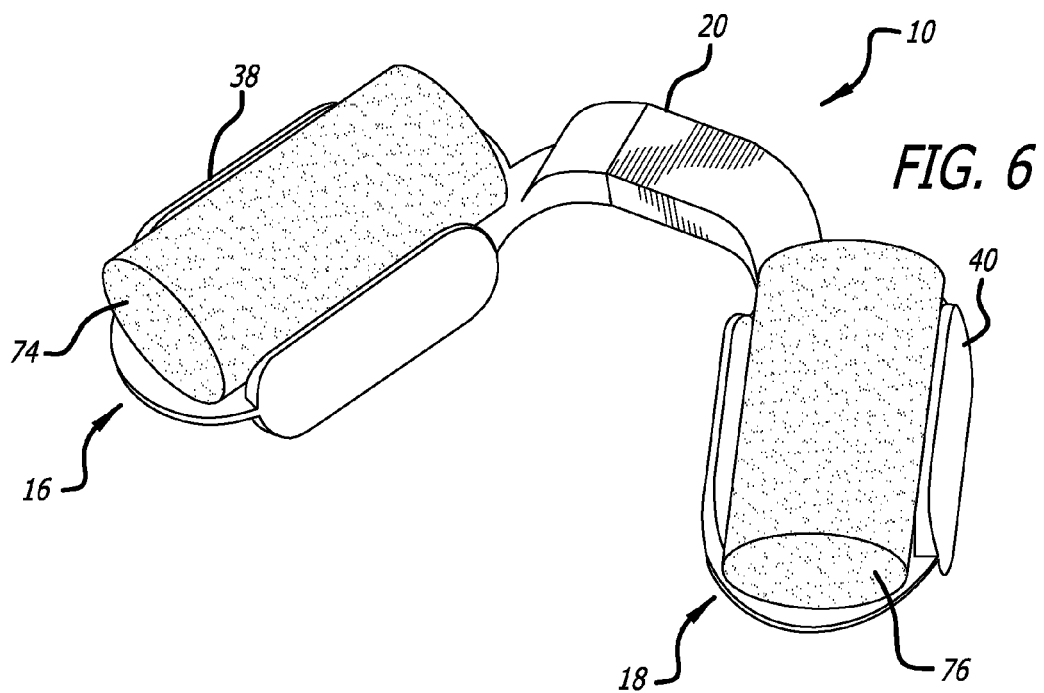
FIG. 6 shows the 2 different epoxies poly vinyl siloxane base and catalyst, like a log divided in half and put into the frame. It can also be stripped across the upper teeth for higher impact sports to help prevent tooth evulsion or fracture.
Figure 7:
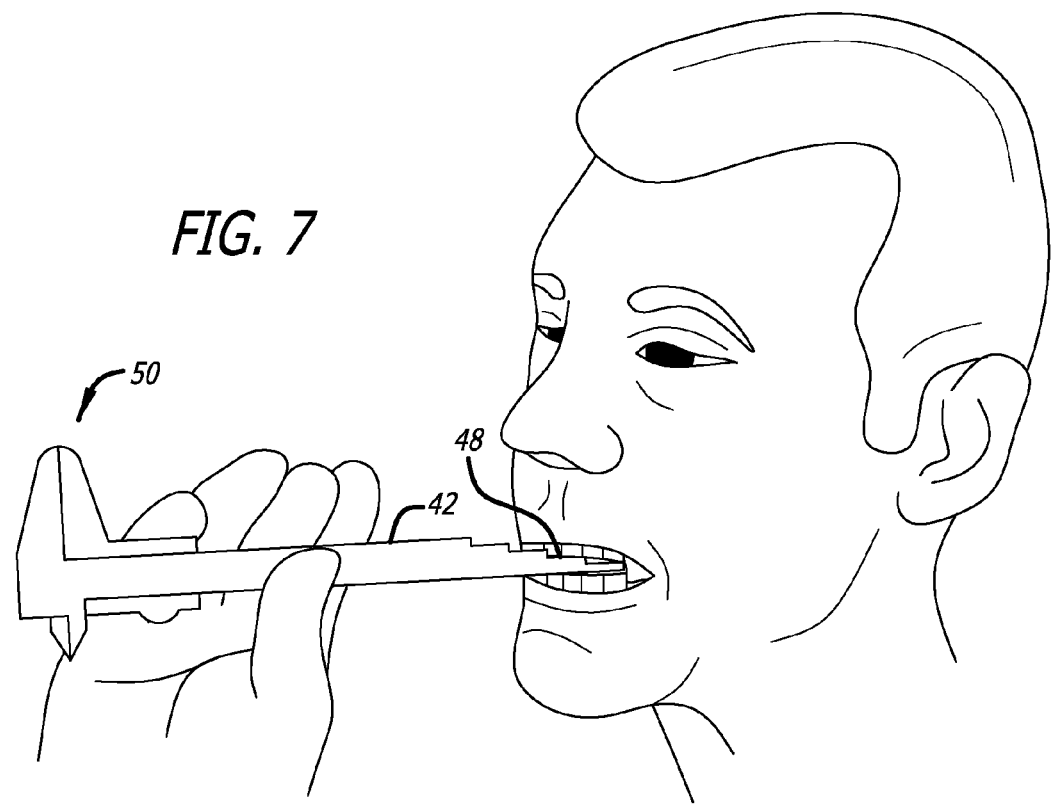
FIG. 7 shows the frame in the mouth and the use of the saw tooth tool to bite down on for a given measurement. This measurement is calculated by the patient. It is used for the patient to help find the optimum position that will get the patient in the zone. This position is pre-calculated and is easy to read from a chart. The patient uses the plastic caliper to determine the width of their central incisor and the length of their teeth together. The chart gives them their "golden vertical". The patient subtracts their vertical from the golden vertical. The amount of mm is how much the open you want to keep the bite open while the silicone sets. That mm step guide is what the patient uses to close into the proper golden vertical.

The figures are illustrated for ease of explanation of the present disclosure only; the extensions of the Figures with respect to number, position, relationship and dimensions of the parts to form the embodiment are within the skill of the art after the following description has been read and understood. The exact dimensions and dimensional proportions to conform to specific force, weight, strength, and similar requirements are within the skill of the art after the following description has been read and understood. The terms such as "inferior," "superior," "anterior," "posterior," "proximal," "distal," "facial," "buccal," "labial," "oral," "lingual," "palatal," "distal," "mesial," and similar positional and/or relative terms are terms that should be understood with reference the structures shown in the drawings and as they used by those skilled in the art.

DETAILED DESCRIPTION OF THE DISCLOSURE

An oral appliance for a user comprises the following components:

A first body is configured to be secured over one or more teeth of a user.

The first body 16 comprises a frame 38 for location about at least one of a molar a premolar of user, a first bite pad 12 between upper teeth and lower teeth.

The first bite pad 12 is molded in the frame while in situ in the mouth of the user and the first bite pad is formed by a PVS material.

The first bite pad 12 is in contact with at least one of a molar, or a premolar of user, and the first bite pad defines an exterior shape of at least a portion of the teeth of a user.

A second body 18 is configured to be secured over one or more teeth of a user.

The second body comprises a frame 40 for location about at least one of a molar, or a premolar of user, a second bite pad 14 between upper teeth and lower teeth.

The second bite pad 14 is molded in the frame while in situ in the mouth of the user and the second bite pad is formed by a PVS material.

The second bite pad 14 is in contact with at least one of a molar, or a premolar of user, and the second bite pad defines an exterior shape of at least a portion of the teeth of a user.

There is a connector 20 between the first frame 38 and the second frame 40 thereby connecting the first body and second body together and forming with the first body and second body the appliance for the user.

Each body of the frame includes pair of side walls 37 and 39; and 41 and 43. One wall is for location inside of a select number of teeth and a second wall is for location outside the select number of teeth. The side walls are slightly bent so that they are concave to follow the contour of the teeth themselves. On the inside of the side walls there are little plastic bumps to facilitate PVS binding with and into the frame.

There is a first joinder component 11 for connecting the side walls 37 and 39; and 41 and 43 and the connector 20. Also each body of the frame includes a second joinder component 13 for connecting the side walls 37 and 39; and 41 and 43 opposite to the first joinder component, and wherein each of the first and second joinders are preformed substantially flat elements for location between the teeth. The joinders sit behind the lower front teeth.

The first joinder component extends between the upper teeth and lower teeth of a user.

The first and second bite pads are, respectively, for location between a molar or premolar. They are formed without a spacer between respective upper and lower molars of the upper teeth and lower teeth. In this sense the frame is hollow.

The bite plates are formed with the PVS as discussed above.

The frame includes respective side walls which extend upwardly over part of the side of the upper molar or premolar, and respective side walls which extend downwardly over part of the side of the lower molar or premolar. The side walls are slightly bent so that they are concave to follow the contour of the teeth themselves. On the inside of the side walls there are little plastic bumps to facilitate PVS binding with and into the frame.

The connector includes two components. One respective component is connected to the first body, and the other respective component is connected to the second body. Each component has a respective free end, and the free ends are releasably connectible together.

The connector also includes multiple sections. One section is connected to the first body and being in a first plane. Another section is connected to the second body and is located in the first plane. There is a third section between the first and second sections, and the third section is located in a plane removed from the first plane of the first and second sections.

The frame for each of the bite pads is formed such that it has two spaced straight lateral wall portions one for location in the interior of the mouth and the other side for location outside the teeth. The two lateral portions can be sufficiently high to protrude beyond the bite pad which is formed. In other situations the height is shorter so that the material forming the pad extends over one or both the walls. The front and the rear of each frame include semicircular joinder portions respectively for joining the two walls together. The semicircular portions would extend over the teeth surface between the top and lower teeth. In some cases there may be only a single joinder member at the forward portion.

A method of creating an oral insert uses the oral appliance. The insert is placed in the mouth of the user to fit with at least one of a molar or a premolar of user. A PVS formulation of a composition of multiple epoxies is placed in position between at least one of a molar or a premolar of user. The PVS is permitted to set and form the insert in situ.

The incisor edge of the upper front tooth and a lower front tooth of a user are aligned substantially edge to edge before having the PVS set.

The system of the disclosure enhances the MORA effect or the neuromuscular zone or the physiological correct position that enables patients to get this burst of strength, better balance, and increased flexibility. This is further described in Mouth Protectors: Give Your Teeth a Sporting Chance, American Dental Association, 1985. Stephen D. Smith, D.M.D., Muscular Strength Correlated to Jaw Posture and the Temporomandibular Joint, New York State Dental Journal, vol. 44, No. 7, August-September 1978. W. B. May, D.D.S., Reduction of Stress in the Chewing Mechanism—Part III. These references are incorporated by reference herein. The disclosed mouthguard brings a patient relatively accurately into this zone. This zone varies on each individual and is spherical in shape like a football. The disclosed kit helps patients achieve the results by finding the sweet spot in the jaw that takes pressure off the central nervous system which results in relatively increased strength.

The use of the device helps each patient differently for different conditions. If the patient bites very far forward (protrusive) it will help sleep by reducing the snore sound and allow patients to sleep better, and reduce sleep apnea.

When the guard is used in a position biting end to end or incisal edge to incisal edge, the guard enhances the sports benefit and minimizes temporomandibular ailments such as headaches, neck pain, and ear and jaw pain. The mouthguard can help re-capture the articulator disc in the condylar jaw that may be out of alignment. Should a disc be off its track it can also be said to be without reduction or non-reduced. Closing the jaw in its natural arc of closure may prevent a disc from becoming non reduced thus keeping it in correctly between the condyle and glenoid fossa.

A dentist using the kit and technique may use a "tens machine" to relax the muscles and allow the patient to close while tensing which will make the disclosed device an orthotic or mouthpiece neuromuscular device. A dentist with a tens machine or a patient with an at-home tens machine can use this prior to mixing the PVS to more fully relax the muscles of the jaw before closing into the unset PVS in the frame. The mandible sits in a sling of muscles. This sling allows the jaw to rest in 6 dimensions. After Tensing for 40 minutes or so, the muscles of the jaw lose their habitual tension and rest at their natural resting length or a place of least electrical activity if measured with an electromyography sensor. In this physiological resting position, the patient gently closes into the wet PVS at the proper vertical dimension and waits 60 seconds in that position until the PVS sets. This is a true neuromuscular position that mimics a sophisticated orthotic produced by a professional dentist.

There are different manners to attain the physiologically correct position of the mouth when the guard is formed in situ.

One method is for the user or patient to swallow while the PVS sets. This allows the jaw to go in all six dimensions: pitch yaw and roll a-p, lateral and up and down. This is a swallow bite that helps de program the muscles in relaxing while the PVS sets. A preferred form of forming the kit is to have the user swallow multiple times while the PVS is setting. This achieves a swallow bite and creates a relaxed state of the lower jaw, and promotes a physiologically correct positioning and forming of the guard for the user's mouth.

Another additive or alternative method uses a tool to for insertion between the incisor edges for facilitating alignment of the incisor edges. The tool includes a saw tooth end, and the end is for insertion between the top and bottom front incisors when forming the appliance. The saw tooth permits for establishing a different selected spacing between the top and bottom front incisors. The spacing is in accordance with the selected saw tooth depth, and is in accordance with attaining a desired appliance. The edges are aligned thereby to attain a position of the golden vertical distance of the incisors.

The golden proportion is the mathematical definition of beauty and form. The proportion is 1 to 1.618. Being in this proportion typically is in alignment with proper function of the body.

The form of how it is calculated for teeth is set out as follows with reference to the following chart.

Golden Vertical

Ideal W:H ratio is 75-80%
H:W ratio is 1.29%
Measure width of centrals
Multiply this by 1.298
Width×1.298 mm=Length
Length×Golden Proportion (1.618)=Golden Vertical
Width of Maxillary Central x1.29=(length) x1.618=Golden Vertical.

The following chart is of use in determining the physiologically correct positions.

| Centrals | Ideal Length | Golden Vertical |
| --- | --- | --- |
| 7 mm | 9 mm | 14.5 mm |
| 7.5 mm | 9.75 mm | 15.75 mm |
| 8 mm | 10.5 mm | 17 mm |
| 8.5 mm | 11 mm | 17.75 mm |
| 9 mm | 11.5 mm | 18.5 mm |
| 9.5 mm | 12.25 mm | 20 mm |
| 10 mm | 13 mm | 21 mm |
| 10.5 mm | 13.5 mm | 22 mm |

Patients can find their own golden vertical and subtract that from their actual vertical. This measurement is how far open is their mouth at the time the silicon will set in the mouth when the patient closes end to end. The plastic caliper on one end and the stepped mm guide on the other assist in the user attaining the physiologically correct position. The chart provides a more exact mathematical measurement. The chart can be used with just the width of central—then golden vertical.

The golden vertical calculations used with the system of the disclosure is simpler by eliminating the middle column of the above chart. Just width of central and then golden vertical can be used by using the number of golden vertical and the patient's own vertical.

Vertical is calculated when patients teeth are together. In such a position the top of front tooth is aligned to bottom of bottom tooth. The golden vertical is subtracted from the user's own vertical to get the amount the bite needs to open. If the number is a negative number, meaning that the patient's actual vertical is greater than the golden vertical, and the patient should close incisal edge to incisal edge.

With these mathematical calculations, the tool and the mm stick of the tool are used to bite on during the setting of the PVS.

This is described in further detail.

Finding this physiological correct position utilizing the disclosed guard is described.

Utilizing the golden proportion concept that there is a mathematical definition for form and function. A proportion that our bodies like to be in which is 1 to 1.618. Utilizing this proportion can help patients find their optimum bite positions. See http://www.goldenmeangauge.co.uk.

The ideal perfect human bite is in golden proportion as the front teeth are in proportion to the lower teeth when the teeth are closed. This measurement is found by measuring the width of a front upper central incisor. From that measurement, there is a mathematical determination to locate the perfect length of the bite (vertical dimension) when the teeth are closed. Most patients are over-closed. They have worn their teeth down over the years. By subtracting their own vertical dimensions of their bites from the golden proportion vertical dimension allows the patient to know how many mm thick their mouth appliance should be.

The disclosed bite stick tool allows the patient to stop their teeth from coming too close together and allowing them to stop in their optimum golden vertical dimension. Once in this position, the patient should swallow as the PVS sets. This allows the jaw to roll in all six of its dimensions at rest.

Examples of Use

A first example is of a person who has worn his teeth halfway down over the years. The user measures the width of his upper front central incisor and finds out that it is 7 mm across. Looking at the disclosed easy to read chart, the user notices that the golden vertical for a central that is 7 mm across is 14.5 mm. The user then measures the vertical distance of his own bite using our plastic boley gauge which is only 12 mm. The user then subtracts the 14.5 mm from the 12 mm of his bite to get 2.5 mm. The 2.5 mm is the distance he wants to stop his bite short when he places the PVS into the hollow holes of our guard instead of closing his bite all the way down to incisal edge to incisal edge.

In a second example the patient should close on their natural arc of closure and stop 1 mm or so before their incisal edges of their teeth come together. Once there, have the patient relax and swallow as the PVS sets.

A kit 30 for forming the oral appliance 10 is also provided. The kit 30 comprises a package 32 wherein there are two different PVS formulations 34 and 36. The PVS formulations are of a nature that their interaction with each other promotes setting of the combination PVS formulations as a PVS final set material.

The kit 30 also includes is a first body 16 or member comprising part of a first frame 38 for location about at least one of a molar a premolar of user to form a first bite pad between upper teeth and lower teeth. The first bite pad is formed by molding it in the first frame 38 while in situ in the mouth of the user and the first bite pad being formed by the PVS material.

The kit 30 also includes a second body 18 or member comprising part comprising a second frame 40 for location about at least one of a molar a premolar of user to form a second bite pad between upper teeth and lower teeth. The second bite pad is molded in the second frame 40 while in situ in the mouth of the user, and the second bite pad being formed by the PVS material.

The kit 30 also includes a connector 20 between the first frame 38 and the second frame 40. This connects the first body 16 and second body 18 together and forming the appliance 10 for the user. The connector can have locks to enable locking in three or more different positions or widths for wider or narrower mandibular arches. This makes the frame a one size fits all universal frame. The locks in the connector can be formed by protruding teeth on one connector components which fit into mating slots or holes in the mating part of the other connector.

The kit 30 includes a tool 42 for insertion between the upper incisor edges 44 and lower incisor edges 46, and is for facilitating alignment of the incisor edges 44 and 46. The tool 42 includes a saw tooth end 48, the end being for insertion between the top and bottom front incisor edges 44 and 46 when forming the appliance 10. The saw tooth end 48 permits for establishing a different selected spacing between the top and bottom front incisors edges 44 and 46. The spacing is in accordance with the selected saw tooth depth, and in accordance with attaining a desired appliance 10.

The kit 30 has the two different PVS substances 34 and 36, the frame portions 38 and 40 of the mouth guard, the caliper end 50 of the tool 42 for measuring teeth to determine how much space is needed. There is an instruction sheet 52 with a link to a video and several pair of gloves 54. The saw tooth end 48 for inserting between teeth when making the molds of the appliance 10.

After taking some measurement with the calipers 50, the saw tooth end 48 is inserted between the front incisors edges 44 and 46 to obtain the "golden vertical" distance. This distance and the saw tooth end 48 of the caliper tool 42 are correlated to the 1 mm, 2 mmm etc. steps on the end 48 of the caliper tool 42.

The first body 16 is configured to be secured over one or more teeth of a user, and the first body 16 comprises a composite structure. The composite structure comprises at least a first bite pad 56, and the first bite pad 56 is in a position to contact at least one of a molar a premolar of user. The inner surface 58 of the bite pad has a shape of at least a portion of the teeth of a user.

The second body 18 is configured to be secured over one or more teeth of a user. The second body 18 comprises a composite structure, and at least a second bite pad 60. The composite structure at the second bite pad 60 is in a position to contact at least one of a molar a premolar of user. The inner surface 62 of the bite pad 60 has a shape of at least a portion of the teeth of a user.

The connector 20 defines a first mounting portion 64 and a second mounting portion 66. The first mounting portion 64 is secured to the first body 16 and the second mounting portion 66 secured to the second body 18.

The connector 20 extends from a buccal edge of the first body 16 and has a first mesial bend. The connector 20 extends from a buccal edge of the first body 16 and has a second mesial bend. An arch 68 of the connector 20 extends between the first mesial bend and the second mesial bend with the first mesial bend and the second mesial bend. The arch 68 of the connector 20 can be location adjacent to one of incisors of the user and the gum line adjacent to the incisors of the user. The connector lies on the lingual of the lower central incisors. When the frame lies passive in the mouth it preferably is not outwardly visible since the connector is behind the front lower teeth.

The process of creating the molded parts of the bite pads 56 and 60 is affected once the measurements are taken and how much space and the size have been determined. There can be two different epoxies 34 and 36. These are mixed together, for instance, between the hands 70 and rolled out like a log 72. The log 72 is then divided in half 74 and 76 and put in the respective frames or trays 38 and 40. The frames or trays 38 and 40 as connected by the connector 20 are placed is in the mouth. Then the saw tooth 48 is used to bite down on for a given measurement as had been obtained by the caliper 50.

Figure 8:
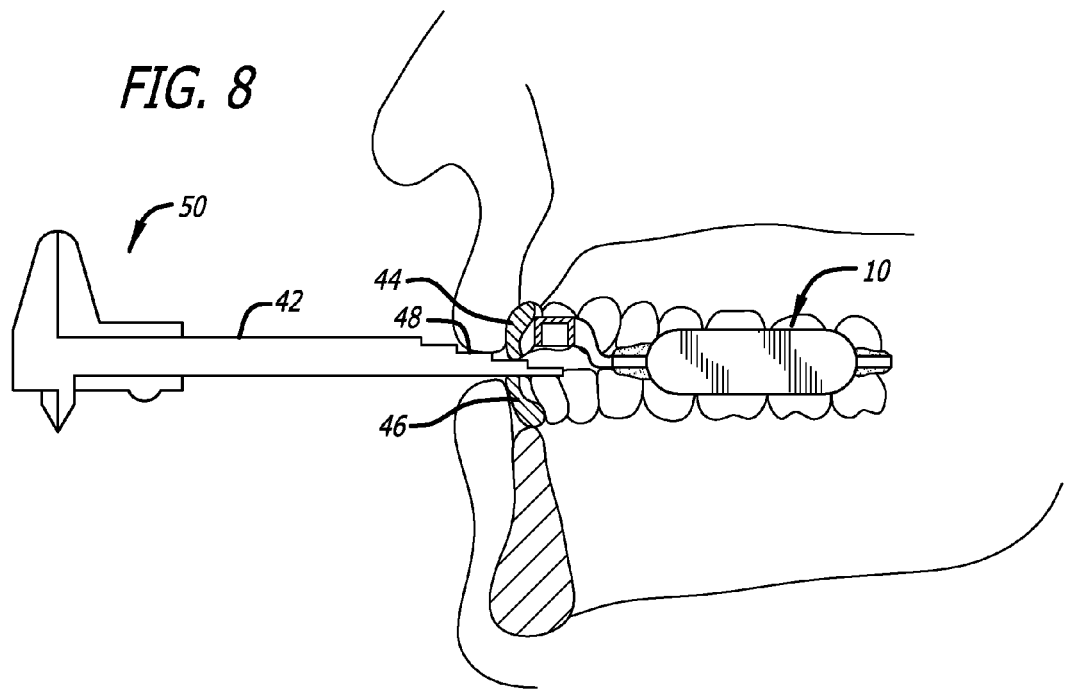
FIG. 8 shows this process of FIG. 7 in cross section and shows the jaw alignment and tooth separation.
Figure 9:
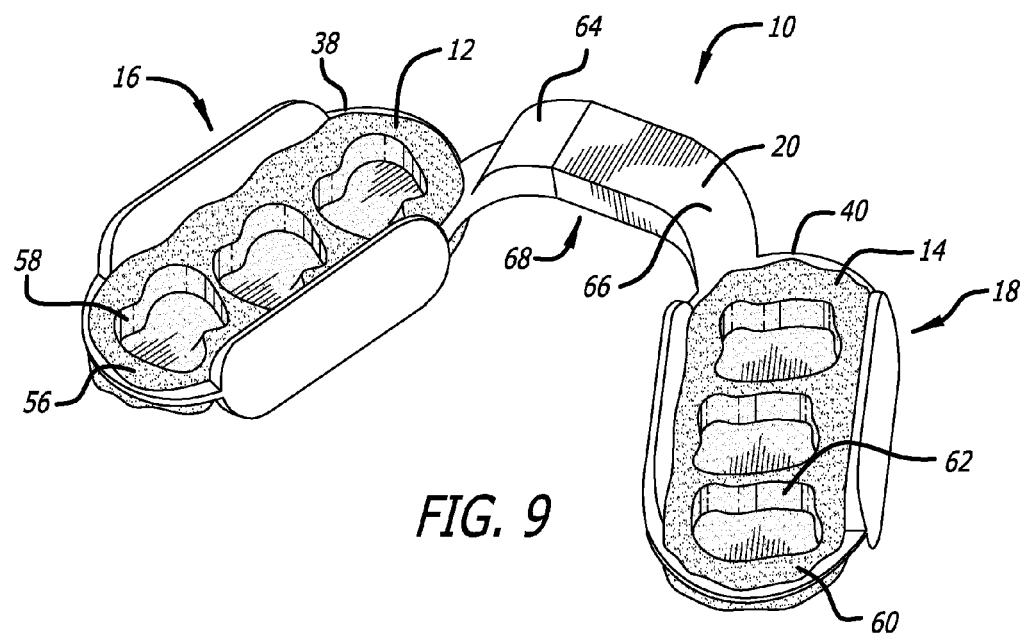
FIG. 9 shows the finished oral appliance product.

FIG. 8 shows this process in cross section and helps show the jaw alignment and tooth separation. FIG. 9 show a finished oral appliance product 10 in a front top perspective view as an exemplary embodiment of an oral appliance 10 to be positioned on the upper teeth a user in accordance with aspects of the present disclosure.

Various embodiments of oral appliances 10 are illustrated throughout the figures for exemplary purposes. The illustrated oral appliance 10 includes the frame 38 with at least a first bite pad 12 and a second bite pad 14 interconnected by a connector 20. The first bite pad 12 may be defined by, secured to, or integral within a first body 16. Similarly, the second bite pad 14 may be defined by, secured to, or integral with a second body 18. The first body 16 and the second body 18 may be configured to secure and/or position the first bite pad 12 and the second bite pad 14 at the desired position relative to the occlusal surface of the teeth.

The bite pads 12 and 14 do not include a spacer in one form of the disclosure. In some other forms of the disclosure there could a spacer element in each of the first and second bodies, the spacer elements extending in part or in whole in the space between the occlusal surfaces of the top and bottom teeth.

The bite pads 12, 14 may be configured to space the occlusal surface of one or more premolars and molars when the teeth of a user are clenched and may be generally configured to reduce or alleviate pressure at the temporomandibular joint when the user's teeth are clenched. The bite pads 12, 14 may also or alternatively be generally configured to protect the teeth and/or temporomandibular joint of a user when the user is subject to a blow to the jaw, head or otherwise receives an impacting force that may travel to or through the jaw. This minimizes the degree of concussion suffered by the user.

The oral appliance 10 may be configured to be received over at least some of the upper teeth or lower teeth of a user. The first body 16 and the second body 18 are interconnected by connector 20 configured to be positioned against the lingual or palatal surface of the gums. The first bite pad 12 and the second bite pad 14 are generally configured to be positioned over at least one of the lower molars on each side of a user's jaw when worn by a user. When the upper teeth and the lower teeth of a user are juxtaposed, the first bite pad 12 and the second bite pad 14 may be positioned between at least some of the upper molars and/or premolars and some of the lower molars and/or premolars. In certain embodiments, the first bite pad 12 and the second bite pad 14 may cover at least a portion of the second premolar and at least a portion of the first molar on each side of the jaw of a user.

The connector 20 secures the first bite pad 12 to the second bite pad 14. The connector 20 may secure the first bite pad 12 to the second bite pad 14 by being secured to the first body 16 and the second body 18 to which the first bite pad 12 and the second bite pad 14 are respectively secured or otherwise integrated. The connector 20 is typically configured to extend as an arch around the lingual or palatal side of the front teeth of a user. In certain embodiments, The connector 20 may extend along or just below the gum line on an oral appliance 10 configured for the lower teeth or along or just above on an oral appliance 10 configured for the upper teeth. This positioning of the connector can reduce the perceived obtrusiveness of the bar within the mouth and can also reduce the impact on a user's speech. By placing the connector on the lingual of the lower front teeth, this allows the lower jaw to be non-obtrusive with the upper teeth. The lower jaw has the freedom to go into a protrusive position if need be and the connector is not seen by the patient.

The frame and/or connector may be made from various metals, metal alloys, various polymers, various laminates, various natural materials or other synthetic materials as known to those skilled in the art.

The components are configured to conform to reduce the obtrusiveness of the oral appliance 10 in the mouth of the user. The portion may include flattened regions to conform to the gums and teeth of a user. The portions may include a textured or otherwise treated surface to assist in the bonding between the material or materials that form the bodies 16, 18 and the connector 20.

The first body 16 and the second body 18 may be composed of one or more layers of materials. One example of this material which can be single material or composition of different components of material is an Exaflex (trademark) putty which is a vinyl polysiloxane impression material. It is a type O Putty made and/or distributed by GC America Inc., Alsip, Ill. 60803. There can be a base material and a catalyst material.

These materials can include ethyl-vinyl acetate (EVA); thermoplastic polyolefin, various ethylene-based elastomers; various hydrocarbon resins (which are may be combined with EVA, thermoplastic polyolefin, or various ethylene-based elastomers), polycaprolactone (which may be combined with EVA), low-density polyethylene, high density poly-ethylene, polycarbonate and/or various polymers, laminates and other materials that will be known by those skilled in the art. The composite material may be a pre-laminated sheet including a layer of polycarbonate bound to a layer of polyester urethane which is available under the trade name Durasoft.® from the Scheu Dental Co. located in Iserlohn, Germany. Typically, these materials are selected with a durometer (hardness) of between 70 A to 96 A or between 55D and 90D.

At least a portion of the inferior surface of the first body 16 and the second body 18 may conform to the shape of the teeth of the user. This can enhance the fit, comfort and retention of the oral appliance 10 in the mouth of a user. At least a portion of a superior surface of the first body 16 and the second body 18 may also be shaped to correspond to the shape of the teeth of a user. In certain aspects, this shape may enhance the comfort and aesthetics of the oral appliance 10.

The first body 16 and the second body 18 each form a mesial body edge. The mesial body edge is typically configured to be positioned at or distal to the canines when the oral appliance is positioned in the mouth of a user. This can reduce the comfort of the device by eliminating coverage of the lingual side of the incisors that can cause irritation to the tongue of users.

The first body 16 and the second body 18 also each form a distal body edge. The distal body edge is typically configured to be positioned at or mesial to the second molar or, when present, the third molar when the oral appliance is positioned in the mouth of a user.

At least a portion of the first body 16 and the second body 18 may define the first bite pad 12 and the second bite pad 14. The bite pads 12, 14 of oral appliance 10 may be configured to at least reduce pressure in the temporomandibular joint as the lower mandible is clenched. In certain aspects, the oral appliance 10 may tend to direct the mandibular condyle downward from the articular fossa in response an attempt by a user to clench their teeth. In other aspects, the oral appliance 10 may tend to direct the mandibular condyle downward and forward from the articular fossa in response an attempt by a user to clench their teeth.

The bite pads 12, 14 are generally configured to define an external occlusal surface to contact at least a portion of the occlusal surface of the opposing teeth and a channel occlusal surface to contact the occlusal surfaces of the teeth relative to which the oral appliance 10 is secured. At least a portion of the channel occlusal surface is coextensive with the channel occlusal surface and may include the characteristics and features of the occlusal surface. The bite pads 12, 14 are generally configured to be positioned adjacent the occlusal surfaces of at least one of the canines, the premolars and the molars with at least one bite pad 12, 14 on each side of a user's mouth. Typically, the bite pads 12, 14 are positioned over the occlusal surfaces of at least one the premolars and at least one of the molars. In other aspects, the bite pads 12, 14 may be solely positioned over the occlusal surfaces of one or more molars.

The mesial body edge of the first body 16 is positioned at mesial of the first premolar and the distal body edge of the first body 16 is positioned at distal of the second molar to position the first body 16 between at least the first premolar and second molar for exemplary purposes. Similarly, the mesial body edge of the second body 18 is positioned at mesial of the first premolar and the distal body edge of the second body 18 is positioned at distal of the second molar to position the second body 18 between at least the first premolar and second molar for exemplary purposes.

The connector 20 extends around the front of the mouth along the lingual surface of the gums just under the gum line. The connector 20 extends away from lingual body edges of the first body 16 and the second body 18 toward or through a transverse plane defined at one or more points along the lingual body edges. The connector 20 further includes a mesial bend to position an arch of the connector 20 at or below the gum line of a user. The arch may be positioned substantially coplanar in a transverse plane defined at one or more points along the lingual body edge of the first body 16 and the second body 18.

The arch may be positioned below a transverse plane defined at one or more points along the lingual body edge of the first body 16 and the second body 18. In embodiments configured for use on the upper teeth, the arch may be positioned above a transverse plane defined substantially at the lingual body edge of the first body 16 and the second body 18.

The disclosed system is an innovative universal fitting frame. The fact that it is hollow over the molar and premolars allows for varied thinness or thickness for our mouth piece. It allows for patients who have uneven thickness from the right side to the left side or from the anterior portion to the posterior portion. It accommodates any inadequacies in the bite and evens them out.

The self-setting PVS allows the user to mix the base and catalyst which helps customize the amount of material that is needed on each side of the frame.

This allows the lower jaw to move into its natural resting position without being restricted by the maxilla (upper jaw) for patients who have deep over-bites. The system allows the jaw to move forward into its natural most comfortable position. It frees the mandible.

It is intended to cover various modifications and similar arrangements included within the spirit and scope of the claims, the scope of which should be accorded the broadest interpretation so as to encompass all such modifications and similar structures. For instance, the distances, spaces, sizes and measurements can vary relative to each other.

The present disclosures provide oral appliances and methods for their manufacture. The figures generally illustrate embodiments of oral appliances and methods for their manufacture in accordance with the present disclosures.

In some other exemplary embodiments of the appliance there are the different features of the bite pads, frames, and connector.

As shown in FIGS. 10A and 10B there is a first alternative oral appliance product and the separable frames used for making the oral appliance product. The PVS formed portions of the appliance product are shown in the frames and the PVS also extends in a channel 78 in part of the connector 20. As such the PVS forms a strip 80 between the bite pads 56 and 60.

Both the top of the bite pads 56 and 60 form indentation surfaces 58 and 62 respectively for the teeth. The under surfaces of the bite pads 56 and 60 form indentation surfaces 82 and 84 respectively for the pads. 56 and 60.

FIGS. 11A and 11B show a second alternative oral appliance product with the separable frames used for making the oral appliance product. In this embodiment the frames 38 and 40 each have two parts forming adjustable side walls 86 and 88 for the frame 38 and side walls 90 and 92 for the frame 40. In this manner the first and second bodies 16 and 18 respectively can be adjusted in size accord to teeth placement of a user. Adjustment can be effected by slots 94 which engage pins extending from the mating parts of the two part frames 38 and 40.

Figure 12A:
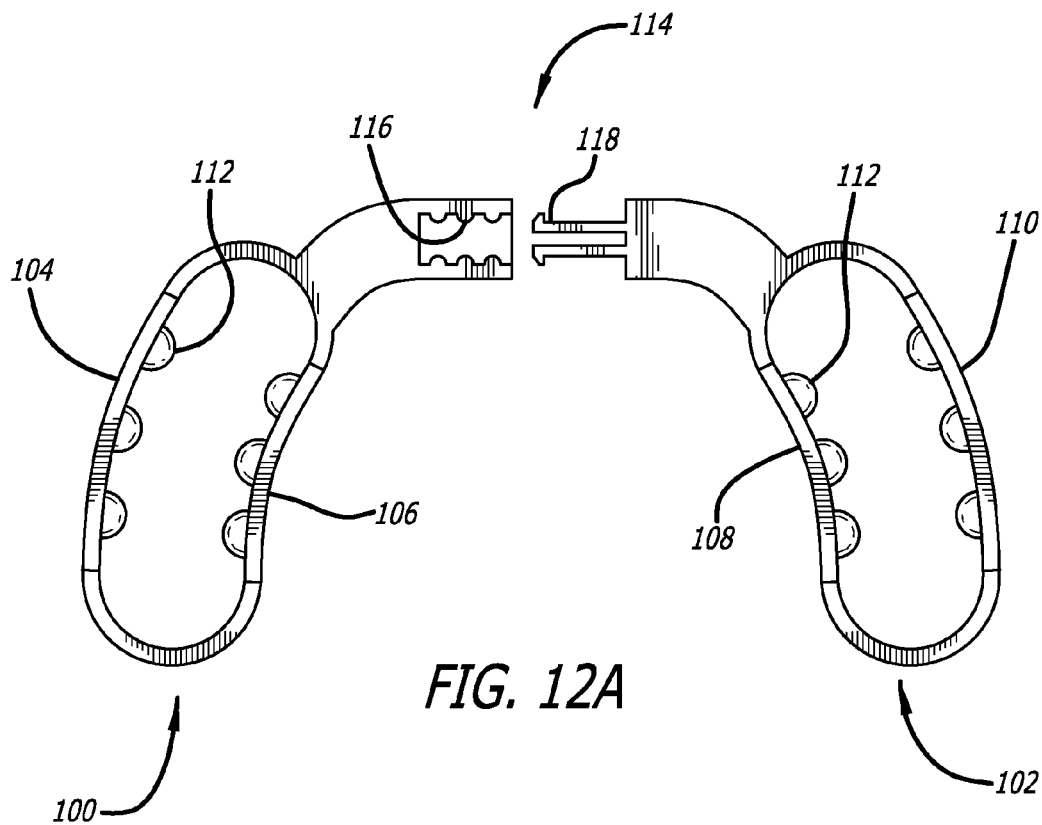
FIGS. 12A and 12B are perspective views showing a multi positional form of the connector with the first and second bodies, and also showing the frame. The connector has a lock formation to permit the connector to take up different positions.
Figure 12B:
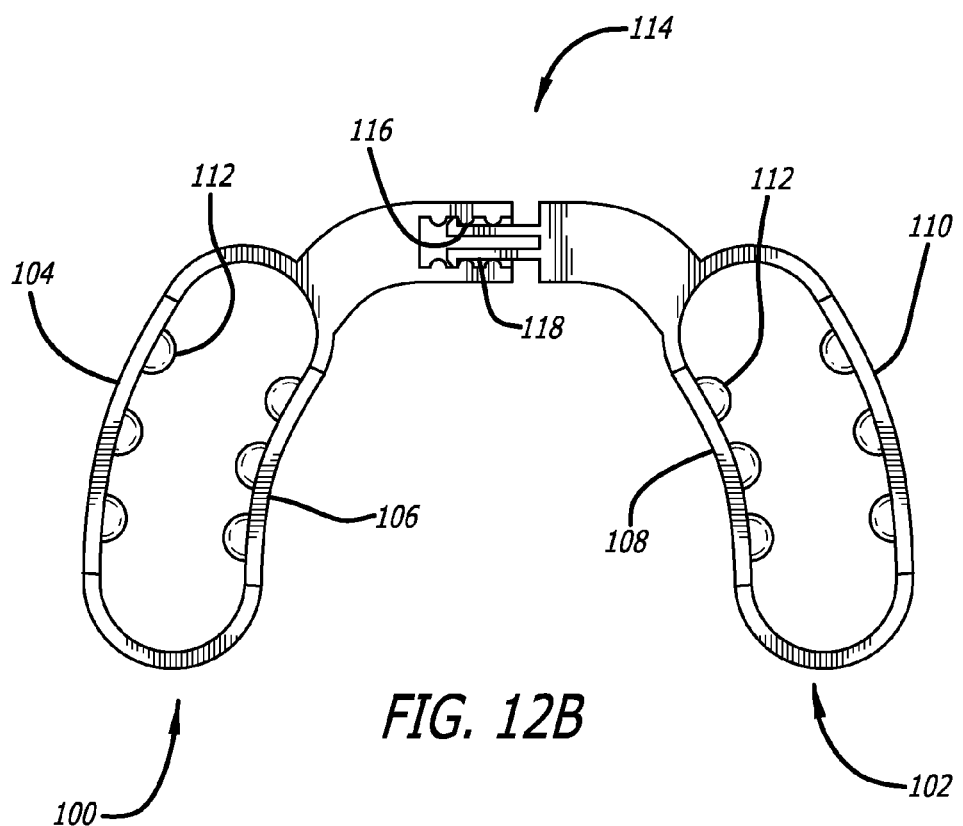

In FIGS. 12A and 12B illustrate a connector 114 which can be located in three different positions with spaced teeth 116 in a first part of the connector which can lock in desired positions with mating teeth 118 in a second part of the connector. The side walls 104, 106 108 and 110 are curved to match the shape of the jaw. There are also spaced projections 112 on the inside faces of the side walls about which the PVS can set. The projections add to the security of the connection and PVS with the sidewalls.

Figure 13:
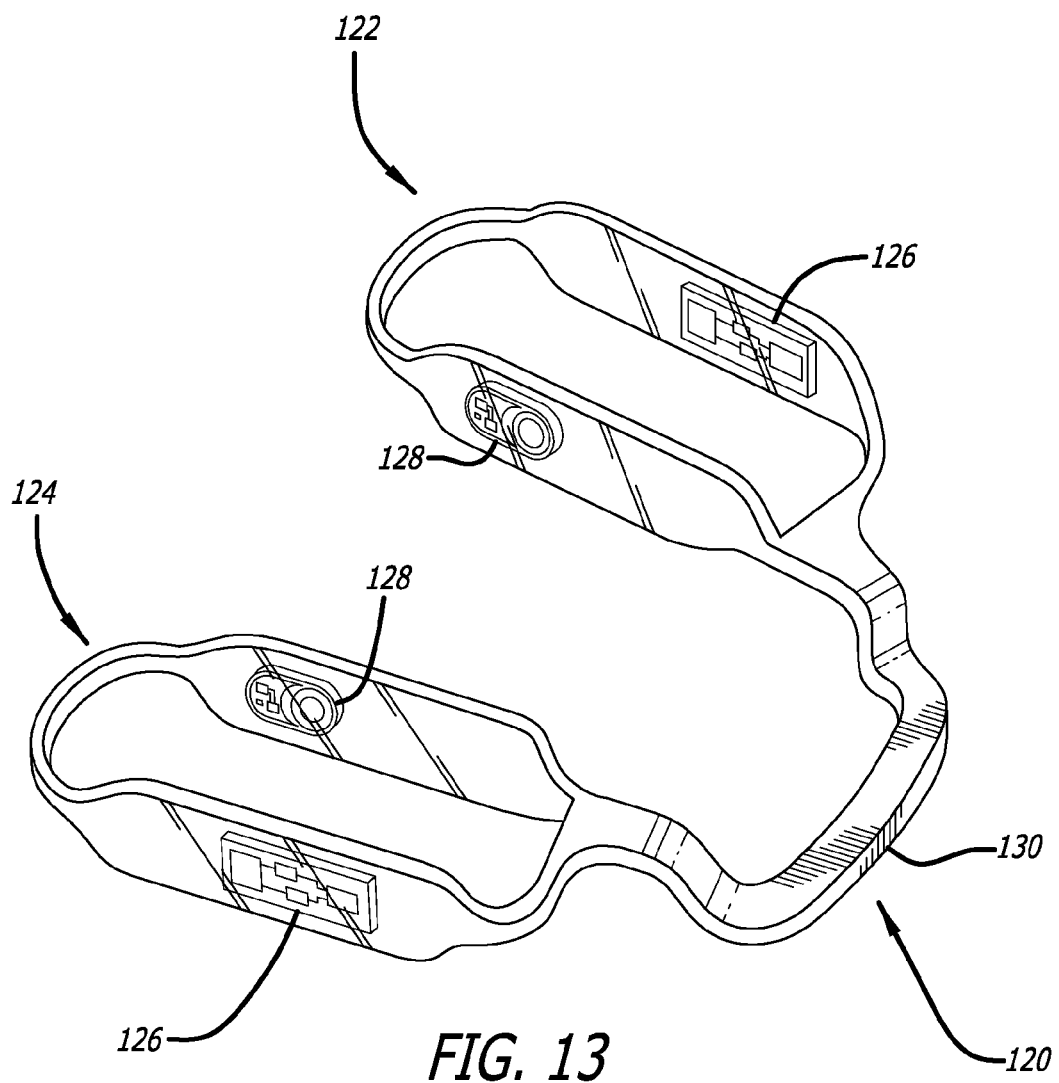
FIG. 13 is a perspective view showing an integrated single piece form of device with the first and second bodies, and also showing the frame.

In FIG. 13 there is shown an integrated single piece oral appliance where the connector is a single piece. There are also sensors 126 and 128 on the side walls which can monitor different physiological conditions in the mouth and or about the teeth. Such conditions can be temperature and different chemical concentrations, force and these can be transmitted by the sensor to a receiver for analysis.

As shown in FIGS. 14A, 14B and 14C there can be a kit formed oral appliances respectively each of three different sizes: small, medium and large. This kit can contain one or more integrated devices of one/or more different sizes and/or include devices of variable widths.

Figure 15A:
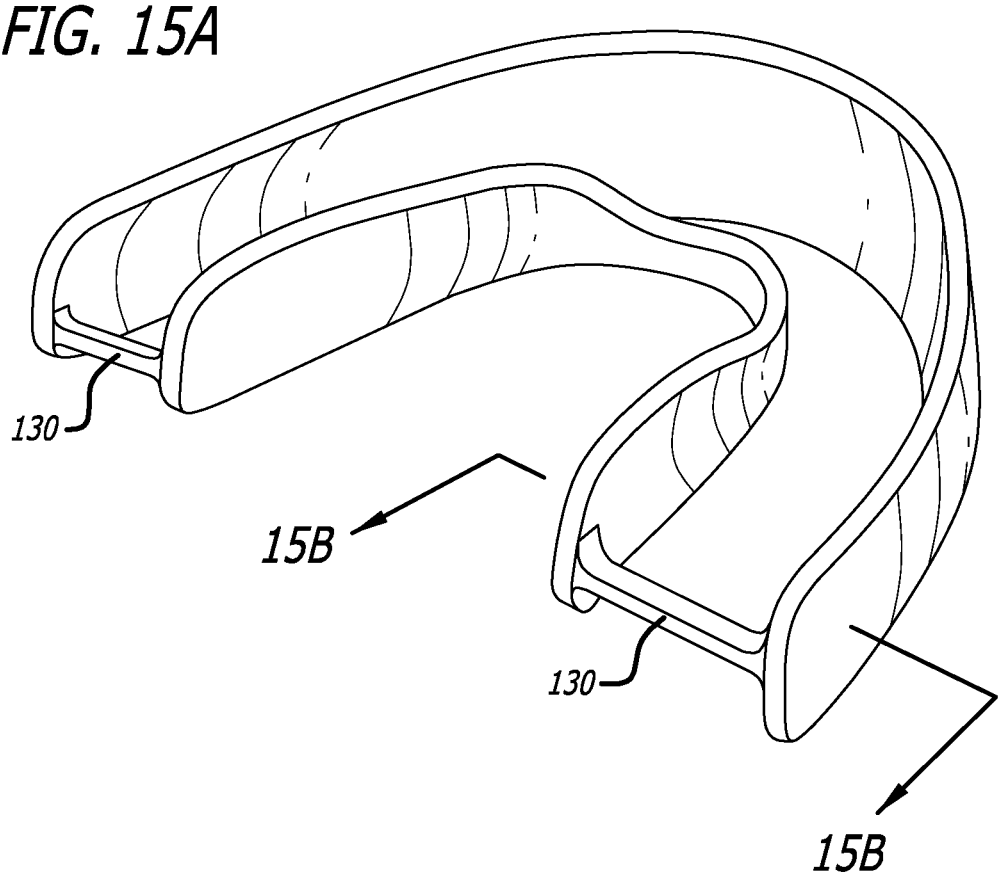
FIG. 15A is a perspective view and FIG. 15B is a cross-sectional view showing an integrated single piece form of device with the first and second bodies which are integrated with and into the hollow frame.
Figure 15B:
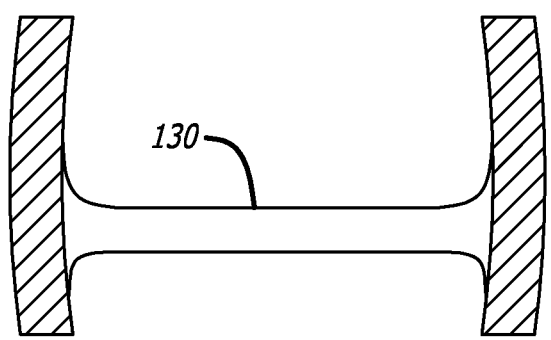

As shown in FIG. 15A and FIG. 15B there is an integrated single piece form of device with the first and second bodies which are integrated with and into the hollow frame which extends from the molars on one side of the jaw to the molars on the other side of the jaw. The two frames are connected by a cross member 130. The walls of the frame are shown relatively more curved to conform to the curved shape of the teeth. In some cases the hollow frame can be formed by two or more components.

In different forms the frame is part of the final oral appliance product 10. In other forms the frame is removed and bite pads and a connecter as shown in FIG. 10A is the oral appliance product 10. The connector 20 can be of a nature that it is an integral single format structure. Alternatively, there can be the two components which are releasable joined through the integrating pair of spaced partly flexible pins 96 in the receiving slot 98.

The particular exemplary embodiments of the oral appliances illustrated in the figures have been chosen for ease of explanation and understanding of the various aspects of the present disclosures. These illustrated embodiments are not meant to limit the scope of coverage but instead to assist in understanding the context of the language used in this specification and the appended claims. Accordingly, variations of oral appliances including claimed aspects of the disclosures different from the illustrated embodiments may be encompassed by the appended claims

The invention claimed is:

1. An oral appliance for a user comprising:
a first body configured to be secured over one or more teeth of a user, the first body comprising a first frame for location about at least one of a molar or a premolar of user, a first bite pad between upper teeth and lower teeth, the first bite pad being adapted to be molded in the frame while in situ in the mouth of the user and the first bite pad being adapted to be formed and adapted to be set in situ by a PVS material, the first bite pad adapted to be in contact with at least one of a molar or a premolar of user, and the first bite pad adapted to define an exterior shape of at least a portion of the upper teeth and the lower teeth of a user;
a second body configured to be secured over one or more teeth of a user, the second body comprising a second frame for location about at least one of a molar or a premolar of user, a second bite pad between upper teeth and lower teeth, the second bite pad being adapted to be molded in the frame while in situ in the mouth of the user and the first bite pad being adapted to be formed and adapted to be set in situ by a PVS material, the second bite pad being in contact with at least one of a molar or a premolar of user, and the second bite pad defining an exterior shape of at least a portion of the upper teeth and the lower teeth of a user;
the respective first frame and the second frame, prior to having the respective bite pads in place being hollow without an intervening spacer between a to and a bottom of each of the respective frames; and
a connector between the first frame and the second frame thereby connecting the first body and second body together and forming with the first body and second body, the appliance for the user, and the connector being adapted for location solely within the mouth, and further being adapted to be located on the inside of the lower teeth.

2. The oral appliance of claim 1 wherein for each body the frame includes pair of side walls, one wall being for location inside of a select number of teeth and the second wall being for location outside the select number of teeth, and a first joinder component for connecting the side walls and the connector.

3. The oral appliance of claim 2 wherein for each body the frame includes second joinder component for connecting the side walls opposite to the first joinder component, and wherein each of the first and second joinders are preformed substantially flat elements for location between the teeth.

4. The oral appliance of claim 3 wherein the first joinder component extends between upper teeth and lower teeth of a user.

5. The oral appliance of claim 2 wherein the first joinder component extends between upper teeth and lower teeth of a user.

6. The oral appliance of claim 2 wherein the first and second bite pads respectively for the molar or premolar are formed without a spacer between respective upper and lower molars of the upper teeth and lower teeth for which the first and second bite plates are formed with the PVS material.

7. The oral appliance of claim 2 wherein each respective side wall is adapted to extend upwardly over part of the side of the upper molar or premolar, and each respective side wall is adapted to extend downwardly over part of the side of the lower molar or premolar.

8. The oral appliance of claim 1 wherein the connector includes two components, one respective component being connected to the first body, and the other respective component being connected to the second body, each component having a respective free end, the free ends being releasably connectible together.

9. The oral appliance of claim 1 wherein the connector includes multiple sections, one section being connected to the first body and being in a first plane, another section being connected to the second body and being in the first plane, and a third section between the first and second section the third section being in a plane removed from the first plane of the first and second sections.

10. The oral appliance of claim 1 wherein the connector between the first frame and the second frame connects with the frame of the first body and the frame of the second body at a location on the frames with the connector adapted for location in part between upper and lower teeth.

11. The oral appliance of claim 1 wherein the first and second bite pads are adapted to be formed solely with the PVS material and without an intervening web in the respective body between the upper and lower teeth.

12. The oral appliance of claim 1 including a sensor on the side wall adapted to monitor physiological conditions in the mouth or about the teeth, such conditions selectively being at least one of temperature, different chemical concentrations and force, and these sensed conditions being for transmittal by the sensor to a receiver for analysis.

13. The oral appliance of claim 1 wherein the appliance is adapted to be formed and set without applying external heat to the first and second bodies, the connector, or the first or second bite pads when they are formed and set.

* * * * *